United States Patent [19]

Sutherland et al.

[11] Patent Number: 5,919,680
[45] Date of Patent: Jul. 6, 1999

[54] PROCESS FOR THE PRODUCTION OF SSC'S VIA EXPANDASE ACTIVITY ON PENICILLIN G

[75] Inventors: John David Sutherland, Osney Island, United Kingdom; Roelof Ary Lans Bovenberg, Rotterdam; Jan Metske van der Laan, Breda, both of Netherlands

[73] Assignee: Isis Innovation Limited, Oxford, United Kingdom

[21] Appl. No.: 08/757,443

[22] Filed: Nov. 27, 1996

Related U.S. Application Data

[60] Provisional application No. 60/007,564, Nov. 27, 1995.

[30] Foreign Application Priority Data

Nov. 27, 1995 [EP] European Pat. Off. .............. 95203259

[51] Int. Cl.$^6$ ........................... C12P 33/10; C12N 15/52; C12N 9/00; C12N 1/21
[52] U.S. Cl. ........................... 435/183; 435/49; 435/69.1; 435/252.3; 435/252.31; 435/320.1; 435/471; 435/479; 536/23.2; 935/10; 935/14; 935/29; 935/60; 935/75
[58] Field of Search ........................... 435/183, 49, 69.1, 435/252.3, 252.35, 471, 479; 536/23.2

[56] References Cited

U.S. PATENT DOCUMENTS

| | | | |
|---|---|---|---|
| 4,003,894 | 1/1977 | Verweij et al. | 540/218 |
| 4,510,246 | 4/1985 | Wolfe et al. | 435/183 |
| 4,536,476 | 8/1985 | Wolfe et al. | 435/183 |
| 4,579,818 | 4/1986 | Wolfe et al. | 435/47 |
| 4,753,881 | 6/1988 | Yeh et al. | 435/183 |

FOREIGN PATENT DOCUMENTS

| | | |
|---|---|---|
| 0 341 892 A2 | 11/1989 | European Pat. Off. . |
| 0 366 354 A2 | 5/1990 | European Pat. Off. . |
| 0 448 180 A2 | 9/1991 | European Pat. Off. . |
| 0 453 047 A1 | 10/1991 | European Pat. Off. . |
| 0 532 341 A1 | 3/1993 | European Pat. Off. . |
| WO 95/02042 | 1/1995 | WIPO . |
| WO 95/04148 | 2/1995 | WIPO . |
| WO 95/04149 | 2/1995 | WIPO . |

OTHER PUBLICATIONS

Aharonowitx, Cohen and Martin, "Penicillin and Cephalospornin Biosynthetic Genes," Annu. Rev. Microbiol. (1992) 46:461–495.

Alvi et al. "Isolation and Identification of a New Cephem Compound from *Penicillium chrysogenum* Strains Expressing Deacetoxycephalosporin C Synthase Activity," The Journal of Antibiotics (1995) 48:338–340.

Baldwin & Abraham "The Biosynthesis of Penicillins and Cephalosporins," Natural Product Reports (1988) 5(2):129–145.

Baldwin et al., "Genetic Engineering of Cephalosporin Biosynthesis," Proceedings of the 7$^{th}$ International Symposium on the Genetics of Industrial Microorganisms (1994) Abstract p. 262.

Blackburn et al., "A Heuristic Approach to the Analysis of Enzymic Catalysis: Reaction of δ–(L–α–Aminoadipoyl . . . ," Biochemistry (1995) 34:7562.

Cantwell et al., "Isolation of deacetoxycephalosporin C from fermentation broths of Penicillium . . . ," Proc. R. Soc. Lond. B (1992) 248:283–289.

Cortes et al., "Purification and Characterization of a 2–Oxoglutarate–linked ATP–independent Deacetoxycephalosporin C Synthase of *Streptomyces lactamdurans*," Journ. of Gen. Microbiol. (1987) 133:3165–3174.

Coque et al., "Characterization and expression in *Streptomyces lividans* of cefD and cefE genes from *Nocardia lactamdurans*: the organization of the cephamycin gene cluster differs from that in *Streptomyces clavuligerus*," Mol. Gen. Genet. (1993) 236:453–458.

Crawford et al., "Production of Cephalosporin Intermediates by Feeding Adipic Acid to Recombinant *Penicillium chrysogenum* Strains Expressing Ring Expansion Activity," Bio/Technology, 13:58–61, (1995).

Ingolia et al., "Beta–Lactam Biosynthetic Genes," Med Res Rev (1989), 9:245–264.

Maeda et al.,"The substrate specificity of deacetoxycephalosporin C synthase ("expandase") of *Streptomyces clavuligerus* is extremely narrow," (1995) 17:231–234.

Cooper, "The Enzymes Involved in Biosynthesis of Penicillin and Cephalosporin; Their Structure and Function," Bioorganic & Med Chem (1993) 1:1–17.

Roach et al., "Crystal structure of Isopenicillin N synthase is the first from a new structural family of enzymes," Naturel (1995) 375:700–704.

Wolfe, S., et al., Science, vol. 226, "Enzymatic approach to syntheses of unnatural beta–lactams", pp. 1386–1392, 1984.

Yeh, W. K., et al., Annals of the New York Academy of Sciences, vol. 672, "Enzymes for epimerization of isopenicillin N, ring expansion of penicillin N, and 3'–hydroxylation of deacetoxycephalosporin C", pp. 396–408, 1993.

Condor, M., et al., Biotechnology '94—Applied Biocatalysis, "Cephalosporin production in *Penicillium chrysogenum*: the application of metabolic engineering to the development of a new biocatalytic process", pp. 20–24.

Primary Examiner—Robert A. Wax
Assistant Examiner—William W. Moore
Attorney, Agent, or Firm—Morrison & Foerster, LLP

[57] ABSTRACT

An overall process for the preparation and recovery of 7-aminodesacetoxycephalosporanic acid (7-ADCA) via enzymatic ring expansion activity on penicillin G, using a *Penicillium chrysogenum* transformant strain expressing modified expandase enzyme.

16 Claims, No Drawings

PROCESS FOR THE PRODUCTION OF SSC'S VIA EXPANDASE ACTIVITY ON PENICILLIN G

This application claims benefit of provisional application Ser. No. 60/007,564 filed Nov. 27, 1996.

FIELD OF THE INVENTION AND BRIEF DESCRIPTION OF THE PRIOR ART

The present invention concerns a biosynthetic process for preparation and recovery of 7-aminodesacetoxycephalosporanic acid (7-ADCA), one of the key intermediates used in the preparation of semi-synthetic cephalosporins (SSC's).

β-lactam antibiotics constitute the most important group of antibiotic compounds with a long history of clinical use. Among this group, the prominent ones are the penicillins and cephalosporins. These compounds are naturally produced by the filamentous fungi *Penicillium chrysogenum* and *Acremonium chrysogenum*, respectively.

As a result of classical strain improvement techniques, the production levels of the antibiotics in *Penicillium chrysogenum* and Acremonium chrysogenum have increased dramatically over the past decades. With the increasing knowledge of the biosynthetic pathways leading to penicillins and cephalosporins, and the advent of recombinant DNA technology, new tools for the improvement of production strains and for the in vivo derivatization of the compounds have become available.

Most enzymes involved in β-lactam biosynthesis have been identified and their corresponding genes been cloned, as can be found in Ingolia and Queener, *Med Res Rev* (1989) 9:245–264 (biosynthesis route and enzymes), and Aharonowitz, Cohen, and Martin, *Ann Rev Microbiol* (1992) 46:461–495 (gene cloning).

The first two steps in the biosynthesis of penicillin in *P. chrysogenum* are the condensation of the three amino acids L-5-amino-5-carboxypentanoic acid (L-a-aminoadipic acid) (A), L-cysteine (C) and L-valine (V) into the tripeptide LLD-ACV, followed by cyclization of this tripeptide to form isopenicillin N. This compound contains the typical β-lactam structure.

The third step involves the exchange of the hydrophilic side chain of L-5-amino-5-carboxypentanoic acid by a hydrophobic side chain by the action of the enzyme acyltransferase (AT). The enzymatic exchange reaction mediated by AT takes place inside a cellular organelle, the microbody, as has been described in EP-A-0448180.

The observation that substantial quantities of desacetoxycephalosporin C (DAOC) can be formed by non-precursed *P. chrysogenum* transformants expressing expandase implies the presence of significant amounts of penicillin N, the natural substrate for expandase, in *P. chrysogenum* (Alvi et al., *J Antibiot* (1995) 48:338–340).

Cephalosporins are much more expensive than penicillins. One reason is that some cephalosporins (e.g., cephalexin) are made from penicillins by a number of chemical conversions. Another reason is that, so far, only cephalosporins with a D-5-amino-5-carboxypentanoyl side chain could be fermented. Cephalosporin C, by far the most important starting material in this respect, is very soluble in water at any pH, thus implying lengthy and costly isolation processes using cumbersome and expensive column technology. Cephalosporin C obtained in this way has to be converted into therapeutically used cephalosporins by a number of chemical and enzymatic conversions.

The methods currently favored in industry to prepare the intermediate 7-ADCA involve complex chemical steps leading to the expansion and derivatization of penicillin G. One of the necessary chemical steps to produce 7-ADCA involves the expansion of the 5-membered penicillin ring structure to a 6-membered cephalosporin ring structure (see for instance U.S. Pat. No. 4,003,894). This complex chemical processing is both expensive and noxious to the environment.

Consequently, there is a great desire to replace such chemical processes with enzymatic reactions such as enzymatic catalysis, preferably during fermentation. A key to the replacement of the chemical expansion process by a biological process is the central enzyme in the cephalosporin biosynthetic pathway, desacetoxycephalosporin C synthase, or expandase.

The expandase enzyme from the bacterium *Streptomyces clavuligerus* was found to carry out, in some cases, penicillin ring expansions. When introduced into *P. chrysogenum*, it can convert the penicillin ring structure into the cephalosporin ring structure, as described in Cantwell et al., *Proc R Soc Lond B* (1992) 248:283–289. The expandase enzyme has been well characterized (EP-A-0366354) both biochemically and functionally, as has its corresponding gene. Both physical maps of the cefE gene (EP-A-0341892), DNA sequence and transformation studies in *P. chrysogenum* with cefE have been described.

Another source for a ring expansion enzyme is the bacterium *Nocardia lactamdurans* (formerly *Streptomyces lactamdurans*). Both the biochemical properties of the enzyme and the DNA sequence of the gene have been described (Cortes et al., *J Gen Microbiol* (1987) 133:3165–3174; and Coque et al., *Mol Gen Genet* (1993) 236:453–458, respectively).

Since the expandase catalyses the expansion of the 5-membered thiazolidine ring of penicillin N to the 6-membered dihydrothiazine ring of DAOC this enzyme would be of course a logical candidate to replace the ring expansion steps of the chemical process. Unfortunately, the enzyme works on the penicillin N intermediate of the cephalosporin biosynthetic pathway, but not or very inefficiently on the readily available inexpensive penicillins as produced by *P. chrysogenum*, like penicillin V or penicillin G. Penicillin N is commercially not available and even when expanded, its D-5-amino-5-carboxypentanoyl side chain cannot be easily removed by penicillin acylases.

It has recently been found that the expandase enzyme is capable of expanding penicillins with particular side chains to the corresponding 7-ADCA derivative. This feature of the expandase has been exploited in the technology as disclosed in EP-A-0532341, WO95/04148 and WO95/04149. In these disclosures the conventional chemical conversion of penicillin G to 7-ADCA has been replaced by the in vivo conversion of certain 6-aminopenicillanic acid (6-APA) derivatives in recombinant *Penicillium chrysogenum* strains containing an expandase gene.

More particularly, EP-A-0532341 teaches the in vivo use of the expandase enzyme in *P. chrysogenum*, in combination with a 5-carboxypentanoyl side chain as a feedstock, which is a substrate for the acyltransferase enzyme in *P. chrysogenum*. This leads to the formation of 5-carboxypentanoyl-6-APA, which is converted by an expandase enzyme introduced into the *P. chrysogenum* strain to yield 5-carboxypentanoyl-7-ADCA. Finally, the removal of the 5-carboxypentanoyl side chain is suggested, yielding 7-ADCA as a final product.

In WO95/04148 and WO95/04149 it has been disclosed that 3'-carboxymethylthiopropionic acid and 3,3'-thiodipropionic acid, respectively, were found to be substrates for the expandase, yielding 2-(carboxyethylthio) acetyl- and 3-(carboxymethylthio)propionyl-7-ADCA.

However, the process of the present invention provides more advantages, because of the high penG biosynthetic capacity of penicillin producing strains and the more favorable process of extraction of phenylacetyl-7-ADCA acid. Furthermore the phenylacetyl side chain of phenylacetyl-7-ADCA is very amenable to enzymatic cleavage, by penicillin G amidases produced by several types of microorganisms yielding 7-ADCA, for instance penG acylase as disclosed in EP-A-0453047.

Various publications have reported the expandase not to accept penicillin G or penicillin V as a substrate for expansion (Baldwin & Abraham, Natural Product Reports (1988) 5(2):129–145; Maeda et al. (1995), *Enzyme and Microbial Technology* (1995) 17:231–234; Crawford et al., *Bio/Technology*, 13:58–61). In contrast to those observations one report mentions an activity of expandase on penicillin G in vitro (Baldwin et al., Proceedings of the 7th International Symposium on the Genetics of Industrial Microorganisms (1994) Abstract p.262).

Recently, the structure of the isopenicillin N synthase (IPNS) enzyme of *A. nidulans* has been determined (Roach, *Nature* (1995) 375:700–704). IPNS and expandase belong to the same family of oxidase enzymes. They share biochemical characteristics and, on the basis of sequence homologies, it has been proposed that structural similarities exist between the two enzymes (Roach et al., supra; Cooper, *Bioorganic Med Chem* (1993) 1:1–17).

The mechanism of IPNS activity has been described in several reports (see, for example, Blackburn et al., *Biochemistry* (1995) 34:7548–7562). It is proposed, from an analysis of the chemistry catalysed by IPNS, that the cysteinyl thiol group of ACV must bind to the ferrous ion at the active site in the enzyme-substrate complex. Given this implicit attachment point between the substrate and the enzyme a large number of conformationally distinct binding modes can be distinguished given the crystallographically determined constraints of the active site. It is therefore not obvious how ACV binds aIPNS and, by inference, the mode of binding of penicillin N to expandase is even less apparent.

DISCLOSURE OF THE INVENTION

The present invention provides an improved process for the preparation and recovery of 7-aminodesacetoxycephalosporanic acid (7-ADCA) by:
 a) transforming a *Penicillium chrysogenum* strain with a modified expandase gene, under the transcriptional and translational regulation of fungal expression signals;
 b) fermenting said strain in a culture medium and adding to said culture medium phenylacetic acid or a salt or ester thereof suitable to yield penicillin G, which is expanded to form phenylacetyl-7-ADCA;
 c) recovering the phenylacetyl-7-ADCA from the fermentation broth;
 d) deacylating phenylacetyl-7-ADCA; and
 e) recovering the crystalline 7-ADCA.
Preferably, step (e) is a filtration step.
Preferably, phenylacetyl-7-ADCA is recovered from the fermentation broth by extracting the broth filtrate with an organic solvent immiscible with water at a pH of lower than about 4.5 and back-extracting the same with water at a pH between 4 and 10.

Moreover, the DNA encoding modified expandase and a recombinant DNA vector comprising the same, functionally linked to the transcriptional and translational control elements of a fungal gene, for instance *Aspergillus nidulans* gpdA gene, and the *Aspergillus niger* glcA gene and host cells transformed with the same, are provided.

In another aspect, the invention is directed to a modified expandase, having an altered amino acid sequence from native expandase and which is capable of converting penicillin G to phenylacetyl-7-ADCA.

In still another aspect, the invention is directed to a method to prepare 7-ADCA by treating penicillin G with said modified expandase so as to convert said penicillin G to phenylacetyl-7-ADCA and deacylating said phenylacetyl-7-ADCA.

DETAILED DESCRIPTION OF THE INVENTION

Modified forms of expandase are useful in converting the readily available penicillin G to the relevant intermediate in the synthesis of 7-aminodesacetoxycephalosporanic acid, or 7-ADCA. Applicants have found that modifications at certain amino acid positions corresponding to those in expandase obtained from *Streptomyces clavuligerus* results in altered substrate specificity such that this conversion is catalyzed by the enzyme. Specifically, mutations at positions in an expandase corresponding to the arginine 74, cysteine 155, proline 157, leucine 159, phenylalanine 264, isoleucine 298, tyrosine 302, arginine 306, or arginine 266 in the enzyme from *S. clavuligerus* result in the desired substrate specificity. By positions "corresponding" to these positions is meant that in any analogous expandase obtained from other organisms, when the amino acid sequence is compared to that of *S. clavuligerus*, homology alignment results in matching the relevant position in the reference expandase to that of the additional example. Thus, for example, as shown below, arginine 74 of *S. clavuligerus* corresponds to arginine 87 of aIPNS; cysteine 155 of the expandase of *S. clavuligerus* corresponds to serine at position 183 of aIPNS and so forth.

In general, the modified forms of expandase can be prepared recombinantly and used to convert penicillin G to the appropriate intermediate using standard in vitro techniques. However, in a preferred embodiment, this process can be conducted in vivo.

In this preferred embodiment, functional gene constructs encoding modified expandase enzyme are used in *P. chrysogenum* for the in vivo expansion of the penicillin G ring structure to form the phenylacetyl acid derivative of a key intermediate in the cephalosporin biosynthesis, 7-aminodesacetoxycephalosporanic acid, or 7-ADCA. This derivative has a chemical composition so as to allow efficient solvent extraction, thus providing an economically attractive recovery process.

Modification of the expandase enzyme is directed at producing mutants which best expand penicillin G in in vitro and/or in vivo context where other penicillins such as penicillin N and isopenicillin N can act as competing substrates. This is an essential feature of the invention given the observation of significant amounts of penicillin N being produced by *P. chrysogenum* and the knowledge that penicillin N is a significantly better substrate than penicillin G for the wild-type expandase. By transforming *P. chrysogenum* with such mutants of expandase, novel *P. chrysogenum* strains can be obtained which have an improved capacity for the prediction of phenylacetyl-7-ADCA.

Transformation of *P. chrysogenum* can, in principle, be achieved by various means of DNA delivery, for example PEG-Ca mediated protoplast uptake, electroporation or particle gun techniques, and selection of transformants. See, for example, Van den Hondel en Punt, "Gene Transfer and Vector Development for Filamentous Fungi," in: Applied Molecular Genetics of Fungi (Peberdy, Laten, Ogden, Bennett, eds.), Cambridge University Press (1991). The application of dominant and non-dominant selection markers has been described (Van den Hondel, supra). Selection markers of both homologous (*P. chrysogenum* derived) and heterologous (non-*P. chrysogenum* derived) origin have been described (Gouka et al., *J Biotechnol* (1991) 20:189–200).

The application of the different transformant selection markers, homologous or heterologous, in the presence or absence of vector sequences, physically linked or not to the non-selectable DNA, in the selection of transformants are well known.

The modified cefE gene is placed under the transcriptional and translational control of fungal (be they filamentous or not) gene control elements. Those elements can be obtained from cloned fungal genes like the *P. chrysogenum* IPNS gene, the β tubulin gene, the *Aspergillus nidulans* gpdA gene, or the *Aspergillus niger* glcA gene.

The ring-expansion reaction, mediated by the modified expandase enzyme is introduced into and expressed in *P. chrysogenum*, for instance in strain Wisconsin 54-1255 (deposited at ATCC under accession number 28089). Other strains of *P. chrysogenum*, including mutants of strain Wisconsin 54-1255, having an improved β-lactam yield, are also suitable.

In summary, the present invention teaches how the activity of a modified expandase enzyme introduced into *P. chrysogenum* can be used to improve the yield of phenylactyl-7-ADCA resulting from the in vivo ring expansion of penicillin G.

In accordance with the present invention the β-lactam intermediate phenylacetyl-7-ADCA is produced in *P. chrysogenum* containing the modified expanded gene by adding phenylacetic acid or a salt or an ester thereof to the medium. Suitable salts are, for instance, those of sodium or potassium. Phenylacetyl-7-ADCA is efficiently recovered from the medium through a simple solvent extraction, for instance, as follows:

The broth is filtered and an organic solvent immiscible with water is added to the filtrate. The pH is adjusted in order to extract the phenyl acetylated cephalosporin from the aqueous layer. The pH range has to be lower than 4.5; preferably between 4 and 1, more preferably between 2 and 1. In this way the cephalosporin is separated from many other impurities present in the fermentation broth. Preferably a small volume of organic solvent is used, giving a concentrated solution of the cephalosporin, so achieving reduction of the volumetric flow rates. A second possibility is whole broth extraction at a pH of 4 or lower. Preferably the broth is extracted between 4 and 1 with an organic solvent immiscible with water.

Any solvent that does not interfere with the cephalosporin molecule can be used. Suitable solvents are, for instance, butyl acetate, ethyl acetate, methyl isobutyl ketone, alcohols like butanol, etc. Preferably butylacetate is used.

Thereafter the phenyl acetylated cephalosporin is back extracted with water at a pH between 4 and 10, preferably between 6 and 9. Again the final volume is reduced drastically. The recovery can be carried out at temperatures between 0 and 50° C., and preferably at ambient temperatures.

The aqueous cephalosporin solution thus obtained is treated with a suitable enzyme in order to remove the phenylacetyl side chain and obtain the desired 7-ADCA. A suitable enzyme for the same is the penicillin G acylase as described in EP-A-0453047, also named penicillin amidase.

Preferably, an immobilized enzyme is used, in order to be able to use the enzyme repeatedly. The methodology for the preparation of such particles and the immobilization of the enzymes have been described extensively in EP-A-0222462. The pH of the aqueous solution has a value of, for example pH 4 to pH 9, at which the degradation reaction of cephalosporin is minimized and the desired conversion with the enzyme is optimized. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilized enzyme is removed by filtration. Another possibility is the application of the immobilized enzyme in a fixed or fluidized bed column, or using the enzyme in solution and removing the products by membrane filtration. Subsequently, the reaction mixture is acidified in the presence of an organic solvent immiscible with water.

After adjusting the pH to about 0.1 to 1.5, the layers are separated and the pH of the aqueous layer is adjusted to 2 to 5. The crystalline 7-ADCA is then filtered off.

The deacylation can also be carried out chemically as known in the prior art, for instance, via the formation of an imino-chloride side chain, by adding phosphorus pentachloride at a temperature of lower than 10° C. and subsequently isobutanol at ambient temperatures or lower.

The following examples are offered by way of illustration and not by way of limitation. The overall approach entails (i) identification of residues of expandase involved in substrate specificity, (ii) construction of mutant expandase proteins in a form easily purified as fusion proteins to maltose-binding-protein (MBP), (iii) assessment of activity towards penicillin N and penicillin G following expression in *E. coli* and purification, (iv) subcloning of mutant expandase genes in *P. chrysogenum* expression vectors and expression of mutant expandase in *P. chrysogenum* and detection of phenylacetyl-7-ADCA formation.

In addition to the foregoing approach, which utilizes in vivo conversion of penicillin G to phenylacetyl-7-ADCA, the modified expandase enzyme can be used in vitro to convert penicillin G into this intermediate. Subsequent deacylation of the phenylacetyl-7-ADCA yields the desired 7-ADCA product. The modified expandase can be prepared recombinantly using the organisms described herein or any suitable host cell. In addition, constructs whereby the modified expandase is secreted into the medium of any suitable recombinant host cell provide a convenient source of this enzyme. The cultures of cells producing the modified expandase can be used directly or the expandase can be recovered, by extraction if necessary, and purified to any desired extent.

The modified expandase for use in this method is preferably modified as compared to the expandase obtainable from a microbial source, such as *Streptomyces clavuligerus*. Modifications of other isopenicillin N synthase enzymes may also be employed.

EXAMPLE 1

Identification of Residues Involved in Substrate Side-Chain Binding

Although the sequence of the C-terminal tail is highly conserved throughout all known IPNS isozymes, this region is highly mobile in the cystal structure.

It is proposed that the absence of a fourth iron-binding residue in the α-ketogluarate dependent oxygenase, DAOCS leaves three open coordination sites, sufficient for oxygen and cosubstrate binding. Generation of the ferryl oxene intermediate by oxidative decarboxylation of α-ketogluarate by this enzyme does not therefore require ligand displacement from iron. It is proposed that these considerations make glutamine 330 the most likely candidate for the aIPNS iron ligand which is displaced by substrate binding. Central to the invention is the proposal that, in the case of aIPNS, upon ACV binding, the L-α-aminoadipoyl side chain of ACV displaces the C-terminal tail of the enzyme (glutamine 330, threonine 331 and a number of preceding residues) by virtue of the similarity between the L-α-aminoadipoyl side-chain of ACV the glutaminyl-threonine and of the tail; specifically the carboxylates in both cases are functionally homologous. In the resting state of the aIPNS enzyme, the carboxylate of the c-terminal threonine residue is in a position to form hydrogen-bonds to arginine 87 and serine 183 and hydrophobic contacts with valine 185 and phenylalanine 285. Upon ACV binding to aIPNS it is proposed that serine 183 and arginine 87 can hydrogen bond to the L-α-aminoadipoyl side-chain carboxylate and that hydrophobic contacts can be made between the methylene groups and amide of the side chain to valine 185 and phenylalanine 285. The relatedness of expandase to aIPNS suggests that the D-α-aminoadipoyl side chain of the substrate penicillin N binds in a similar fashion to expendase as does the L-α-aminoadipoyl side chain of ACV to aIPNS. At the heart of the invention is the proposal that the D-α-aminoadipoyl side chain of penicillin N will be bound by amino acid residues of expandase that are homologous to the amino acid residues of aIPNS involved in binding the L-α-aminoadipoyl side chain of ACV in addition to other residues that can be identified by examination of the aIPNS crystal structure using the aforementioned substrate-binding model. Residues of *Streptomyces clavuligerus* expandase so identified include, but are not restricted to arginine 74 (homologous to arginine 87 of aIPNS), cysteine 155 (homologous to serine 183 of aIPNS), proline 157 (homologous to valine 185 of aIPNS), leucine 159 (homologous to isoleucine 187 of aIPNS), phenylalanine 264 (homologous to phenylanaline 285 of aIPNS), isoleucine 298 (homologous to leucine 317 of aIPNS), tyrosine 302 (homologous to leucine 321 of aIPNS), arginine 306 (homologous to isoleucine 325 of aIPNS) and arginine 266 (homologous to aspargine 287 of aIPNS). Mutation of these residues individually or in combination will alter the relative binding of penicillin N and penicillin G to expandase in the ground state and subsequent intermediates and transition states for the expansion of these penicillins to DAOC and phenylacetyldesacetoxycephalosporin, respectively. Mutations at the aforementioned positions of expandase will increase the expansion of penicillin G, decrease the expansion of penicillin N and/or increase the relative ratio of penicillin G to penicillin N expansion in a competitive scenario. Many benefits accrue to a process involving in vivo expansion of penicillin G to phenylacetyl-7-ADCA as described in a patent application entitled "Process for the production of 7-ADCA via expandase activity on penicillin G" and filed on Jun. 2, 1995 with the European Patent Office. The wild type expandase accepts penicillin N as its normal substrate with conflicting reports concerning the acceptance of penicillin G as a substrate. In order to improve penicillin G as an isolated substrate it is necessary to improve $v_{max}$ and, in a context where the concentration of penicillin G is non-saturating, to lower the $K_m$. This is not only the case when penicillin G is an isolated substrate but also when penicillin G is a substrate in the presence of other penicillins, in the first place penicillin N, but also isopenicillin N. In the microbody location of *P. chrysogenum* cefE transformants precursed with phenylacetic acid, the expandase enzyme can act on penicillin N in competition with penicillin G. The relative and absolute amounts of each penicillin expanded depend on the ratio of the individual rates which can be broken down into an equation of the form:

$$\frac{\text{rate of expansion of penicillin } G = V^G = V^G\text{max}_{[G]} K^N_M}{\text{rate of expansion of penicillin } N = V^N = V^N\text{max}_{[N]} K^G_M}$$

where $V^G\text{max}$ and $V^N\text{max}$ correspond to the maximum enzyme velocities, $K^N_M$ and $K^G_M$ are the Michaelis constants, and [G] and [N] are the concentrations of penicillin G and penicillin N respectively. Mutations at positions of the expandase listed below which result in an increase of the ratio of $V^G:V^N$ are part of the invention. The specificity changes required can result from any single or multiple mutant that has values of $v_{max}$ and/or $K_M$ for either or both substrates altered in any way such as to increase the ratio of $V^G:V^N$ in vitro or the relative yield of phenylacetyl-7-ADCA compared to DAOC from a phenylacetate derivative precursed fermentation of a strain of *P. chrysogenum* transformed with the mutant cefE gene.

EXAMPLE 2

Construction of Mutants a) General techniques for gene cloning and manipulation are well described in Sambrook et al., *Molecular Cloning, A Laboratory Manual*, Cold Spring Harbour, USA (1989).

b) Vector construction:

A chlorampenicol gene cartridge (Pharmacia, HindIII cartridge) is blunt-ended by treatment with Klenow fragment and four dNTPs and ligated to ScaI linearized pMAL-c2 (New England Biolabs) then used to transform competent *E. coli* cells to chloramphenicol resistance. Resultant clones are restriction mapped with NcoI, ApaI and other enzymes and a plasmid in which the direction of transcription of the chloramphenicol resistance gene is the same as that of the malE gene is designated pAJL100. A linker prepared by self-annealing of the palindromic oligonucleotide, AL5 (5'TAC CGA ATT CGG3') is ligated to NdeI linearized pNM88 (Morgan et al., *Bioorg Med Lett* (1994) 4:1595–1600) and the resulting ligation is sanitized by digestion with NdeI before being used to transform *E. coli*. Resultant clones are restriction mapped by digestion with EcoRI, SalI and other enzymes and a plasmid giving the anticipated restriction pattern is designated pAJL103. The *Streptomyces clavuligerus* cefE gene is subcloned as an EcoRI/SalI fragment from pAJL103 into the corresponding polylinker sites of pAJL100 giving pAJL104 which is characterized by restriction mapping with ApaI, BglI, EcoRI, ScaI and other enzymes.

c) Expression in *E. coli*:

Expression of the malE-cefE gene fusion is achieved by induction of a culture of *E. coli* NM554[pAJL104] with IPTG. Induced cells are lysed by treatment with lysozyme followed by sonication and released protein is quantitated by Bradford assay. Purification of the MBP-expandase fusion protein is achieved by application of crude cellular lysates to an amylose column, washing and subsequent elution with buffer containing maltose to give a protein of approximately 77 kDa molecular weight as assessed by SDS-PAGE against molecular weight standards. MBP-DAOCS fusion is assayed for bioactivity using penicillin N as a substrate using reverse-phase HPLC and hole-plate bioassay against super sensitive *E. coli* in the presence of penicillinase. Active protein results in zones of lysis on bioassay plates and a new product with the same retention time as synthetic DAOC on reverse phase HPLC with a variety of buffer conditions and monitoring at 220 and 254 nm. MBP-DAOCS fusion is assayed for bioactivity using penicillin G as a substrate using reverse-phase HPLC and 500 Mhz 'H NMR spectroscopy with confirmatory sample spiking in both cases.

d) Mutagenesis of expandase gene:

Uracil-containing single-stranded pAJL104 DNA is obtained from cultures of *E. coli* BW313[pAJL104] following superinfection with helper phage M13 K07. This uracil-containing single-stranded pAJL104 DNA is used in mutagenesis experiments in which 5'-phosphorylated synthetic oligonucleotides are annealed and extended in the presence of T7 DNA polymerase, T4 DNA ligase, dNTPs and ATP. Following second-strand synthesis the reactions are used to transform competent *E. coli* NM554 or XL1 Blue to chloramphenicol resistance. Resultant clones are restriction mapped or sequenced to confirm the presence of the desired mutation. As examples of mutants constructed in this manner:

Mutation of arginine 74 (arginine 87 in aIPNS):

The R74F mutation is introduced using the phosphorylated primer: 5'ACC ATG TTT CGC GGC TTC ACC3'. Resultant clones are mapped by digestion with SacII, NcoI and other enzymes and the plasmid giving the anticipated fragments is designated pAJL211. The loss of a SacII site in pAHL211 relative to pAHL104 confirms the introduction of the TTT codon encoding phenylalanine in pAHL211.

Mutation of cysteine 155 (serine 183 in aIPNS):

The C155L mutation is introduced using the phosphorylated primer: 5'GAG GCC TTC CTC GAC CTC GAG CCG CTG CTG CGG3'. Resultant clones are mapped by digestion with XhoI, NcoI and other enzymes and the plasmid giving the anticipated fragments is designated pAJL201. The XhoI site in pAJL201 confirms the presence of the CTC codon encoding leucine.

Mutation of proline 157 (valine 185 in aIPNS):

The P157F, P157V, P157G and P157A mutations are introduced using the phosphorylated primer mixture: 5'GCC TTC CTT GAC TGC GAA NNN CTT CTC CGT TTT CGC TAC TTC CCG3'. Where N represents a mixture of G, A, T and C. Resultant clones are mapped by digestion with XmnI, NcoI and other enzymes and plasmids having the extra XmnI site are analyzed further by digestion with EcoRI, ScaI, StuI and Eco47III. Plasmids having an added Eco RI site are designated pAJL230; the added XmnI and EcoRI sites confirm the presence of a TTC codon encoding phenylalanine. Plasmids having an added ScaI site are designated pAJL231; the added XmnI and ScaI sites confirm the presence of a GTA codon encoding valine. Plasmides having an added StuI site are designated pAJL232; the added XmnI and StuI sites confirm the presence of a GGC codon encoding glycine. Plasmids having an added Eco47III site are designated pAJL233; the added XmnI and Eco47III sites confirm the presence of a GCG codon encoding alanine.

Mutation of arginine 266 (asparagine 287 in aIPNS):

The R266N mutation is introduced using the phosphorylated primer: 5'CC TCC AGT GTG TTC TTT TTA AAT CCC AAC GCG GAC TTC3'. Resultant clones are mapped by digestion with DraI, NcoI and other enzymes and the plasmid giving the anticipated fragments is designated pMJS 1. The introduction of a fifth DraI site confirms the presence of an AAT codon encoding asparagine.

EXAMPLE 3

Characterization of Mutants

The mutants are characterized by HPLC analysis of expansion reactions of penicillin N and penicillin G both individually and in mixtures of differing proportions and amounts. DAOC and phenylacetyldeacetoxycephalosporin are identified by retention times using several different buffers and elution conditions with monitoring at 220 and 254n, and by confirmatory sample spiking. 500 Mhz 1H nmr analysis is also used to confirm the nature of products by comparison with synthetic standards. As examples the following data are obtained:

The R266N mutant is found to expand penicillin N and penicillin G individually less well than the wild-type expandase. In mixtures comprising penicillin N and G, the R266N mutant displays a higher ratio of $V^G:V^N$ than the wild type expandase.

The R74F mutant is found to expand penicillin N poorly and penicillin G very poorly. In mixtures comprising penicillin N and penicillin G, penicillin N is expanded very poorly and penicillin G at the bottom of detection.

The C 155L mutant is found to expand penicillin N well and penicillin G poorly relative to the wild-type expandase. In mixtures containing penicillin N and G, penicillin N expansion is inhibited by penicillin G even though the latter is then a very poor substrate.

These examples demonstrate that mutations in these positions affect the ratio of $V^G:V^N$.

EXAMPLE 4

Fermentative Production of Phenylacetyl - 7-ADCA and Detection of the Same

*P. chrysogenum* strain Wisconsin 54-1255 (ATCC 28089), is used as the host strain for the expandase expression cassettes, but other strains of *P. chrysogenum* might be used as well.

The expression cassettes used are derived from pGSETA and pGSEWA, containing the *S. clavuligerus* expandase gene under the control of *A. nidulans* gpdA gene transcriptional and translational regulatory signals. The construction of pGSETA and pGSEWA is described in detail in PCT/EP94/02543. The wild-type expandase sequence in pGSEWA and GSETA is replaced by the modified expandase sequence by exchange of inserts from the pAJL104 derivatives containing expandase mutations. This is done by using a modified PCR procedure optimized for GC rich DNA (Dutton et al *Nucleic Acids Res* (1993) 21:2953–2954) using oligonucleotide primers: 5'T TCA GAA TTC CAT ATG GAC ACG ACG GTG CCC3' and 5'GCT TGC ATG CAT GTC GAC CTA TGC CTT GGA TGT3' to amplify the insert, by restriction digestion sequentially with NdeI and NsiI and subcloning of the obtained fragment into pGSETA and pGSEWA digested with the same enzymes. The fidelity of the PCR and subcloning processes is verified by restriction enzyme mapping and sequence analysis.

Transformation of protoplasts with modified expandase cassettes is done using the Ca-PEG procedure (Gouka et al., supra). Subsequent transformant selection conditions are as described in PCT/EP94/02543 and EP94201869.1. The *A. nidulans* amdS gene is used as fungal selection marker, as described in EP94201869.1. It is well known in the art that procedures for protoplast preparation and regeneration may differ slightly depending on the particular *P. chrysogenum* strain used.

Transformants are purified and may be analyzed for presence of the expandase cassette by using a PCR screening technique for fungal colonies (Seth, *Fungal Genetics Newsletter* (1991) 38:55). Selected transformants are further analyzed by Southern blot analyses of chromosomal DNA, digested with a restriction enzyme with a 6 bp recognition sequence like EcoRI, and hybridization with an expandase gene specific probe according to methods well known in the art (Sambrook et al., supra).

Conidiospores of selected transformants are inoculated at $2.10^6$ conidia/ml into a seed medium consisting of(g/l): glucose, 30; $(NH_4)_2SO_4$, 10; $KH_2PO_4$, 10; trace element solution I ($MgSO_4.7H_2O$, 25; $FeSO_4.7H_2O$, 10; $CuSO4.5H2O$, 0.5; $ZnSO4.7H2O$, 2; $Na_2SO_4$, 50; $MnSO_4.H_2O$, 2; $CaCl_2.2H_2O$, 5), 10 (ml/l) (pH before sterilization 6.5).

The seed culture is incubated for 48–72 hours at 25° C. and subsequently used to inoculate 10–20 volumes of a production medium containing (g/l) lactose 80; maltose, 20; $CaSO_4$, 4; urea, 3; $MgSO_4.7H_2.O$, 2; $KH_2PO_4$, 7; NaCl, 0.5; $(NH_4)_2SO_4$, 6; $FeSO_4.7H_2O$, 0.1; trace element solution II ($CuSO_4.5H_2O$, 0.5; $ZnSO_4.7H_2O$, 2; $MnSO_4.H_2O$, 2; $Na_2SO_4$, 50) 10 (ml/l (pH before sterilization 5.5–6.0). After inoculation with the seed culture, a 10% phenylacetic acid solution, adjusted to pH 7.0 with KOH, is added to the fermentation to a final concentration of 0.1–0.5%. The incubation is then continued at 25° C. at 220 rpm for another 72–120 hours.

At the end of the fermentation the mycelium is removed by centrifugation or filtration and phenylacetyl-7-ADCA is detected by high performance liquid chromatography (HPLC). The HPLC system consisted of the following Spectra Physics components: P1500 solvent delivery system, As 1000 injector, UV1000 variable wavelength detector (set at 260 mm) and a ISM 100 integrator or similar. The stationary phase is a Chrompack Chromspher C 18 column. The mobile phase consists of 75% phosphate buffer pH 2.6 and 25% acetonitrile. The products are quantitated by comparison to a standard curve of phenylacetyl-7-ADCA and penicillin G. The identity of the phenylacetyl-7-ADCA is established by 600 Mhz NMR of a deutero-chloroform solution obtained by acid extraction of the culture filtrate. The resonances of the phenylacetyl-7-ADCA in the acid extract proved to be identical with those of a synthetic sample.

We claim:

1. A modified pencillin expandase gene encoding a mutant pencillin expandase having an altered substrate specificity as compared to the corresponding wild-type pencillin expandase said modification comprising a substitution at one or more selected sites corresponding to a residue position in penicillin expandase of *Streptomyces clavuligerus* selected from the group consisting of arginine 74, cysteine 155, proline 157, leucine 159, phenylalanine 264, isoleucine 298, tyrosine 302, arginine 306 and arginine 266.

2. The modified pencillin expandase gene of claim 1 comprising one or more mutations selected from the group consisting of R74F; C155L; P157F; P157V; P157G; P157A; and R266N.

3. An expression system which comprises the modified pencillin expandase gene of claim 1 operably linked to control sequences for the expression of said gene.

4. Host cells modified to contain the expression system of claim 3.

5. The host cells of claim 4 which are of a microorganism.

6. The microorganism host cells of claim 5 which are cells of *Penicillium chrysogenum*.

7. A method to produce a modified pencillin expandase which method comprises culturing the cells of claim 4 under conditions wherein said gene is expressed to produce said pencillin expandase.

8. The method of claim 7 which further comprises recovering said pencillin expandase from said culture.

9. A method for preparing 7-aminodesacetoxycephalosporanic acid (7-ADCA) which method comprises treating penicillin G with the culture of claim 7 to produce the intermediate phenylacetyl 7-ADCA.

10. A method for preparing 7-aminodesacetoxycephalosporanic acid (7-ADCA) which method comprises treating penicillin G with the recovered pencillin expandase of claim 8 to produce the intermediate phenylacetyl 7-ADCA.

11. The process of claim 9 which further includes hydrolyzing the phenylacetyl-7-ADCA produced.

12. The process of claim 10 which further includes hydrolyzing the phenylacetyl-7-ADCA produced.

13. An improved process for the preparation and recovery of 7-aminodesacetoxycephalosporanic acid (7-ADCA) by:

a) transforming a *Penicillium chrysogenum* strain with a modified pencillin expandase gene as defined in claim 1 under the transcriptional and translational regulation of fungal expression signals;

b) fermenting said strain in a culture medium and adding to said culture medium phenylacetic acid or a salt or ester thereof suitable to yield penicillin G, which is expanded to form phenylacetyl-7-ADCA;

c) recovering the phenylacetyl-7-ADCA from the fermentation broth;

d) deacylating phenylacetyl-7-ADCA; and e) recovering the crystalline 7-ADCA.

14. The process of claim 13 wherein step (e) is a filtration step.

15. The process of claim 13, wherein step (c) is a filtration step, and by extracting the broth filtrate with an organic solvent immiscible with water at a pH of lower than about 4.5 and back-extracting the same with water at a pH between 4 and 10.

16. The process of claim 13 wherein the pencillin expandase gene is derived from *Streptomyces clavuligerus* or *Norcardia lactamdurans*.

* * * * *